US009498527B2

(12) United States Patent
Fukasaka et al.

(10) Patent No.: US 9,498,527 B2
(45) Date of Patent: Nov. 22, 2016

(54) VACCINE COMPOSITION (71) Applicants: NITTO DENKO CORPORATION, Osaka (JP); OSAKA UNIVERSITY, Osaka (JP)

(72) Inventors: Masahiro Fukasaka, Osaka (JP); Arimichi Okazaki, Osaka (JP); Daisuke Asari, Osaka (JP); Mitsuhiko Hori, Osaka (JP); Shizuo Akira, Osaka (JP); Osamu Takeuchi, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 13/856,002

(22) Filed: Apr. 3, 2013

(65) Prior Publication Data
US 2013/0266612 A1    Oct. 10, 2013

(30) Foreign Application Priority Data
Apr. 4, 2012    (JP) ................................. 2012-085839

(51) Int. Cl.
*A61K 39/39* (2006.01)
*A61K 39/145* (2006.01)
*A61K 39/12* (2006.01)
*A61K 39/00* (2006.01)

(52) U.S. Cl.
CPC ............... *A61K 39/39* (2013.01); *A61K 39/12* (2013.01); *A61K 39/145* (2013.01); *A61K 2039/5252* (2013.01); *A61K 2039/541* (2013.01); *A61K 2039/542* (2013.01); *A61K 2039/55561* (2013.01); *A61K 2039/55572* (2013.01); *A61K 2039/575* (2013.01); *C12N 2710/00034* (2013.01); *C12N 2760/16034* (2013.01); *C12N 2760/16134* (2013.01)

(58) Field of Classification Search
None
See application file for complete search history.

(56) References Cited

U.S. PATENT DOCUMENTS

| | | |
|---|---|---|
| 2005/0203051 A1 | 9/2005 | Karaolis et al. |
| 2005/0276813 A1 | 12/2005 | Muhlradt et al. |
| 2006/0040887 A1 | 2/2006 | Karaolis |
| 2008/0044438 A1 | 2/2008 | Ostroff et al. |
| 2008/0112974 A1 | 5/2008 | Czerkinsky et al. |
| 2008/0286296 A1 | 11/2008 | Ebensen et al. |
| 2009/0162344 A1 | 6/2009 | Soma et al. |
| 2009/0169609 A1 | 7/2009 | Ebensen et al. |
| 2010/0150952 A1* | 6/2010 | Stayton et al. ............ 424/193.1 |
| 2010/0310602 A1 | 12/2010 | Reed et al. |
| 2012/0156240 A1 | 6/2012 | Anderson et al. |
| 2013/0089570 A1 | 4/2013 | Ouaked et al. |

FOREIGN PATENT DOCUMENTS

| | | |
|---|---|---|
| EP | 1 782 826 | 5/2007 |
| JP | 8-198902 | 8/1996 |
| JP | 8-245702 | 9/1996 |
| JP | 2003-519669 | 6/2003 |
| WO | 94/20070 A1 | 9/1994 |
| WO | 01/51082 | 7/2001 |
| WO | 2005/087238 | 9/2005 |
| WO | 2007/061102 | 5/2007 |
| WO | 2007/109564 | 9/2007 |
| WO | 2010/141861 | 12/2010 |
| WO | 2011/005769 | 1/2011 |
| WO | 2011/151431 | 12/2011 |
| WO | WO 2011151431 A1 * | 12/2011 |
| WO | 2012/024632 A2 | 2/2012 |

OTHER PUBLICATIONS

Scheepers et al. Protection of mice against an influenza virus infection by oral vaccination with viral nucleoprotein incorporated into immtmostim afing complexes. Med Microbiol Immunol (1994) 183:265-278.*
Kohchi et al. Applications of lipopolysaccharide derived from Pantoea agglomerans (IP-PA1) for health care based on macrophage network theory. J Biosci Bioeng. Dec. 2006;102(6):485-96.*
Chen et al. Active Synthesis of Hemagglutinin-Specific Immunoglobulin A by Lung Cells of Mice That Were Immunized ntragastrically with Inactivated Influenza Virus Vaccine. Journal of Virology, Jul. 1987, p. 2150-2154. vol. 61, No. 7.*
Cho et al. Enhanced humoral and cellular immune responses after sublingual immunization against human papillomavirus 16 L1 protein with adjuvants. Vaccine. Mar. 19, 2010;28(14):2598-606. Epub Jan. 28, 2010.*
Stills H.F. Adjuvants and Antibody Production: Dispelling the Myths Associated with Freund's Complete and Other Adjuvants. ILAR Journal. 2005. vol. 46, Issue 3, p. 280-293.*
Hebishima et al. Oral Administration of Immunopotentiator from Pantoea agglomerans 1 (IP-PA1) Improves the Survival of B16 Melanoma-Inoculated Model Mice. Exp. Anim. 60(2), 101-109, 2011.*
Wang et al. [Mechanism of the effect of LPSp on the production of anti-HBs in mice]. [Article in Chinese]Xi Bao Yu Fen Zi Mian Yi Xue Za Zhi. Jun. 2007;23(6):559-61.*
Inagawa et al. Oral administration of lipopolysaccharides for the prevention of various diseases: benefit and usefulness. Anticancer Res. Jul. 2011;31(7):2431-6.*
McAleer et al. Educating CD4 T cells with vaccine adjuvants: lessons from lipopolysaccharide. Trends in Immunology, 2010, vol. 31:429-435.*
Libanova et al., *Vaccine*, vol. 28, No. 20, p. 3625, 2010 (XP027000089) and Libanova et al., *Vaccine*, vol. 28, No. 10, pp. 2249-2258, 2010 (XP026924763).

(Continued)

*Primary Examiner* — Nick Zou
(74) *Attorney, Agent, or Firm* — Greenblum and Bernstein, P.L.C.

(57) ABSTRACT

An intraorally administrable vaccine composition useful to be a preventive or therapeutic agent for infectious diseases, and effectively induces a systemic immune response or a mucosal immune response is provided. A vaccine composition for administration to the oral cavity of a human or an animal, the vaccine composition containing at least one antigen derived from an infectious disease, and at least one selected from the group consisting of a toll-like receptor 4 (TLR4) agonist, a toll-like receptor 2/6 (TLR2/6) agonist, and cyclic dinucleotide, or a derivative or salt thereof.

11 Claims, 7 Drawing Sheets

(56) References Cited

OTHER PUBLICATIONS

Ebensen et al., *Vaccine*, vol. 29, No. 32, pp. 5210-5220, 2011 (XP028239815).
Extended European Search Report issued with respect to patent family member EP App. No. 13001690.0, dated Jun. 3, 2013.
Office Action issued with respect to Japanese application No. 2013-073406, mail date is May 13, 2014.
J. Allergy Clin. Immunol, 2008, vol. 121, pp. 368-374.
Immunobiol., 1992, vol. 184, pp. 372-383.
Japanese Office Action issued with respect to Japanese Application No. 2013-073406 with English translation thereof, mail date is Jan. 28, 2014.
PLOS one, 2011, vol. 6, No. 11, e26973.
J. Immunol., 2011, vol. 186, Meeting Abstract Supplement 106.17.
Japanese Society for Immunology SOKAI/GAKUJUTSU SHUKAI KIROKU (Annual meeting records), 2005, vol. 35, p. 17, S11-4.
Eur. J. Immunol., 2003, vol. 33 pp. 1548-1556.
Japanese Journal of Bacteriology, 2006, vol. 61, No. 1, p. 147, III-G-2.
Virus Report, 2008, vol. 5, No. 1, pp. 74-81.
Explanation of Circumstances Concerning Accelerated Examination for Japanese Application. No. 2013-073406.
Wang et al., "A study of adjuvant effect and safety of LPSp on rabies vaccine" Chongging Yixue, 2011, vol. 40, pp. 3643-3645, 3649.
Wang et al., "Effects of pantoea agglomerans lipopolysaccharide on the immune effects of two kinds of rabies vaccine" Shiyong Yixue Zazhi, 2011, vol. 27, pp. 2333-2335.
Ohta et al., "Contribution of the mannan O side-chains to the adjuvant action of lipopolysaccharides" Immunology, 1987, vol. 60, pp. 503-507.
Hebishima et al., "Oral Administration of Immunopotentiator from Pantoea agglomerans 1 (IP-PA1) Improves the Survival of B16 Melanoma-Inoculated Model Mice" Exp. Anim., 2011, vol. 60, pp. 101-109.
Japanese Society for Immunology SOKAI/GAKUJUTSU SHUKAI KIROKU (Annual meeting records), 2007, vol. 37, pp. 159, 2-D-W24-15-O/P.
Song et al., "Sublingual vaccination with influenza virus protects mice against lethal viral infection" Proc. Natl. Acad. Sci. USA, 2008, vol. 105, No. 5, pp. 1644-1649.
Taniguchi et al., "Utility and Safety of LPS-based Fermented Flour Extract as a Macrophage Activator" Anticancer Research, 2009, vol. 29, pp. 859-864.
European Office Action issued with respect to application No. 13001690.0, mail date is Oct. 14, 2014.
Wangxue chen et al., "Vaccine", vol. 28, 2010, pp. 3080-3085.
Chinese Office Action issued with respect to application No. 201310117955.0, mail date is Nov. 30, 2015.
European Search Report issued with respect to application No. 16000035.2, mail date is Mar. 14, 2016.
Jory R. Baldridge et al., "Monophosphoryl lipid A enhances mucosal and systemic immunity to vaccine antigens following intranasal administration", Vaccine 18, 2000, pp. 2416-2425.
Noel K. Childers et al., "Adjuvant Activity of Monophosphoryl Lipid A for Nasal and Oral Immunization with Soluble or Liposome-Associated Antigen", Infection and Immunity, vol. 68, No. 10, Oct. 2000, pp. 5509-5516.
Summons to attend oral proceedings for European application No. 13001690.0, mail date is May 12, 2015.
Chinese Office Action issued with respect to application No. 201310117955.0, dated Aug. 24, 2016.

\* cited by examiner

VACCINE COMPOSITION

TECHNICAL FIELD

The present invention relates to a sublingually administrable vaccine composition useful to be a preventive or therapeutic agent for infectious diseases. The present invention particularly relates to a vaccine composition capable of effectively inducing a systemic immune response and a mucosal immune response when at least one selected from the group consisting of a toll-like receptor 4 (TLR4) agonist, a toll-like receptor 2/6 (TLR2/6) agonist, and cyclic dinucleotide, or a derivative or salt thereof is sublingually administered as an adjuvant together with an antigen derived from an infectious disease.

BACKGROUND ART

Currently, the commercial vaccine preparations are mostly available in the injection form. The injection form vaccine induces the immune response (IgG antibody production) in blood (systemic) but does not induce the mucosal immune response (IgA antibody production), and thus prevents the post-infection pathogen growth but has a problem in the protection against the pathogen infection by mucosal route.

Under the circumstances, the vaccination via mucosal route has been drawing attention in recent years. In particular, the development of a vaccine containing an influenza virus as an antigen for mucosal administration (transnasal administration) has been in a high profile.

The mucosal administration vaccine induces the systemic immunity (IgG antibody production) and also induces the mucosal immunity (IgA antibody production). The IgA antibody does not strictly discriminate the pathogen type of a disease to be targeted, is adaptable to ever-changing pathogen epidemic every year and is thus considered to be effective for the pandemic prevention.

One of the reasons for the transnasal administration vaccine to attract attention is that the antigen administration to the gastrointestinal mucosa is susceptible to the influences of gastric juice and proteases which are hardly evitable, whereas the antigen administration to the transnasal mucosa is free of these influences. Additionally, there is an antigen-recognition tissue called NALT on the nasal cavity mucosa which is beneficial for immune response. This is another reason for the transnasal administration vaccine to gain interests.

However, the antigen administration to the nasal cavity mucosa, while being highly effective, have had drawbacks in that it is most likely to cause critical adverse effects such as acute encephalopathy, or the like; the transnasal administration per se is cumbersome and difficult to practice on the elderly, infant, or the like; and the stable effect is not assured due to physical factors such as nasal mucus, or the like.

On the other hand, there have also been many attempts to induce the systemic immunity and mucosal immunity via oral administration of an antigen through the gastrointestinal mucosa (intestines), and the like, after swallowing. The concern here is how the antigen breakdown caused by the gastric juice or proteases is prevented. To solve the problem, techniques have been developed to neutralize the gastric juice by a large content of an antacid, or to protect an antigen using coating techniques such as microspheres, or the like.

However, the development was practically successful only on vaccines intrinsically highly stable in the gastric juice such as live attenuated poliovirus vaccine and live attenuated rotavirus vaccine.

Alternatively, an allergy vaccine is an example of the oral administration preparation to induce an immune response via the oral cavity mucosa (particularly sublingual mucosa) delivery without swallowing. This vaccine is termed as sublingual immunotherapy (SLIT) and works by continuously administering sublingually a plant-derived extract containing a protein to be an allergy antigen (allergen) to boost the immunotolerance against the allergen and reduce the allergy reaction. In recent years, SLIT is now widely accepted in Europe and many products are available in the market today.

The therapy using such a preparation which induces the immune response via the oral cavity mucosa route, particularly the sublingual mucosa route, is the focus of attention because it provides better patient's QOL and has a lower risk of anaphylactic shock, critical adverse effect, than the conventional therapy which required the subcutaneous injection of an allergen (subcutaneous immunotherapy).

However, SLIT has been to use preparations only for boosting a specific immunotolerance, but has been not a therapy to activate the immunity. The oral cavity mucosa is generally not likely to develop immunity, and the activation of immunity, even if the immunotolerance is developed, has been considered to be difficult.

Examples of the induction of the mucosal immunity and systemic immunity via the oral cavity mucosa route, particularly the sublingual mucosa route, are reported including the following.

OVA-specific systemic immune response (IgG production) and OVA-specific mucosal immune response (IgA production) are proposed to have been confirmed when OVA used as an antigen and cholera toxin used as an adjuvant were administered sublingually (see, for example, Patent Literature 1). However, in the proposal, highly neurotoxic cholera toxin was used as the adjuvant and the safety issue was left to be cleared.

Using OVA as an antigen and 3 de-O-acylated monophosphoryl lipid A, a TLR4 agonist, as an adjuvant and administering them sublingually have been proposed to bring about OVA-specific systemic immune response (IgG production) and OVA-specific mucosal immune response (IgA production) as well (see, for example, Patent Literature 2). In this proposal, a TLR4 agonist was sublingually administered as an adjuvant, however, no example regarding an antigen derived from an infectious disease was presented and the versatility of the effect to the antigen type was not evident. Additionally, the comparatively large doses of OVA being 80 to 160 µg and 3 de-O-acylated monophosphoryl lipid A being 20 to 40 µg are not practical when considering the safety.

A proposal on a method for synthesizing glucopyranosyl lipid, a synthetic adjuvant, (see, for example, Patent Literature 3) also describes the mucosal immune response induction by the mucosal administration of an antigen in combination with the adjuvant. The inductions of serum IgG and IgA in a nasal wash are also proposed by the administration of MALP-2, a TLR2/6 ligand, together with β-galactosidase used as an antigen to the nasal cavity of a mouse (see, for example, Patent Literature 4). However, no example regarding an antigen derived from an infectious disease or administration thereof to the oral cavity mucosa was presented, and thus the versatility of the effect was not evident. Using c-di-GMP or c-di-AMP, cyclic dinucleotide, as an adjuvant together with β-galactosidase as an antigen and intranasally administering them to a mouse have been also proposed to bring about the induction of serum IgG (see, for example, Patent Literature 5), however, the proposal does not mention the IgA induction via transnasal administration and no example regarding an antigen derived from an infectious disease or administration thereof to the oral cavity mucosa was presented, and thus the versatility of the effect was not evident.

CITATION LIST

Patent Literature

Patent Literature 1: U.S. Patent Application Serial No. 2008/0112974
Patent Literature 2: JP 2003-519669 T
Patent Literature 3: U.S. Patent Application Serial No. 2010/0310602
Patent Literature 4: U.S. Patent Application Serial No. 2005/0276813
Patent Literature 5: U.S. Patent Application Serial No. 2008/0286296

SUMMARY OF INVENTION

Technical Problem

Under the current circumstances described above, the present invention has an object to provide a sublingually administrable vaccine composition useful to be a preventive or therapeutic agent for infectious diseases, and effectively induces a systemic immune response or a mucosal immune response.

Solution to Problem

The present inventors conducted extensive studies to solve the above problem and found that a systemic immune response and a mucosal immune response are effectively induced when at least one selected from the group consisting of a toll-like receptor 4 (TLR4) agonist, a toll-like receptor 2/6 (TLR2/6) agonist, and cyclic dinucleotide, or a derivative or salt thereof is orally administered, particularly, sublingually administered, as an adjuvant together with an antigen derived from an infectious disease, whereby the present invention was accomplished.

More specifically, the present invention relates to a vaccine composition for administration to the oral cavity of a human or an animal, the vaccine composition comprising: at least one antigen derived from an infectious disease, and at least one selected from the group consisting of: a toll-like receptor 4 (TLR4) agonist, a toll-like receptor 2/6 (TLR2/6) agonist, and cyclic dinucleotide, or a derivative or salt thereof.

In the vaccine composition of the present invention, the antigen derived from an infectious disease is preferably an influenza virus-derived antigen.

The influenza virus-derived antigen is preferably hemagglutinin protein.

The influenza virus-derived antigen is preferably an inactivated whole virus.

The toll-like receptor 4 (TLR4) agonist preferably comprises at least one selected from the group consisting of: lipopolysaccharide, or salt thereof, and monophosphoryl lipid, or salt thereof.

The lipopolysaccharide, or salt thereof is preferably derived from *Escherichia coli, Salmonella, Pantoea, Acetobacterium, Zymomonas, Xanthomonas* or *Enterobacter*; and the monophosphoryl lipid, or salt thereof is preferably monophosphoryl lipid derived from *Salmonella* or synthetic glucopyranosyl lipid.

The toll-like receptor 2/6 (TLR2/6) agonist comprises preferably diacylated lipopeptide, or a derivative or salt thereof.

The diacylated lipopeptide preferably comprises $Pam_2CSK_4$, MALP-2, FSL-1, or a derivative or salt thereof.

The cyclic dinucleotide preferably comprises c-di-GMP, c-di-AMP, or a derivative or salt thereof.

In the vaccine composition of the present invention, the administration to the oral cavity is preferably administration to the sublingual mucosa.

The vaccine composition of the present invention preferably induces a mucosal immune response and a systemic immune response, and the mucosal immune response is antigen-specific IgA antibody production, and the systemic immune response is antigen-specific IgG antibody production and antigen-specific cell-mediated immune production.

Hereinafter, the present invention is described in detail.

The vaccine composition of the present invention contains at least one antigen derived from an infectious disease.

The above antigen derived from an infectious disease refers to any substances targeted by the immune response developed in a test organism. The above antigen derived from an infectious disease may also be the target of the immune response (e.g., aging of immunocompetent cells, cytokine production, antibody production, etc.) at the contact with the immunocompetent cell.

The antigen derived from an infectious disease used in the present invention is not limited insofar as an antigen is an infectious pathogen or derived from an infectious pathogen.

The disease developed from the above infectious pathogen is not limited and examples include viral diseases caused by the infection of viruses such as adenovirus, herpesvirus (e.g., HSV-I, HSV-II, CMV or VZV), poxviruses (e.g., variola or vaccinia, or orthopoxviruses such as molluscum contagiosum, or the like), picornaviruses (e.g., rhinovirus or enterovirus), orthomyxoviruses (e.g., influenza viruses), paramyxo viruses (e.g., parainfluenza virus, mumps virus, measles virus, respiratory syncytial virus (RSV)), coronaviruses (e.g., SARS), papovaviruses (e.g., papilloma virus which causes genital warts, common warts or plantar warts), hepadnaviruses (e.g., hepatitis B virus), flaviviruses (e.g., hepatitis C virus or dengue virus), or retroviruses (e.g., lentiviruses such as HIV, or the like), and the like; bacterial diseases caused by the infection of bacteria such as *Escherichia, Enterobacter, Salmonella, Staphylococcus, Shigella, Listeria, Aerobacter, Helicobacter, Klebsiella, Proteus, Pseudomonas, Streptococcus, Chlamydiaceae, Mycoplasma, Pneumococci, Neisseria, Clostridium, Bacillus, Corynebacterium, Mycobacterium, Campyrobacter, Vibrion, Serratia, Providencia, Chromobacterium, Brucella, Yersinia, Haemophilus*, or *Bordetella*, and the like; fungus diseases such as *Chlamydia, Candidiasis, Aspergillosis, Histoplasmosis, Cryptococcal Meningitis*, to begin with, but not limited thereto; *Malaria, Pneumocystis carinii pneumonia, Leishmaniasis, Cryptosporidiosis, Toxoplasmosis, Trypanosomal* infection, and the like.

In the present invention, the antigen derived from an infectious disease is preferably an influenza virus-derived antigen.

The influenza virus used herein refers to a RNA enveloped virus belonging to *Orthomyxoviridae* and having a particle diameter size of about 100 nm, and is classified into Types A, B and C based on the antigenicity of internal protein thereof. The influenza virus is composed of a core of an internal nucleocapsid surrounded by a virus envelope having a lipid bilayer structure or of ribonucleic acid (RNA) associated with nucleoprotein, and an external glycoprotein. The inner layer of the above virus envelope is consisted mainly of matrix proteins and the outer layer is consisted mostly of lipid materials derived from a host cell. The RNA of the influenza virus has a segmental structure. Additionally, influenza worldwide pandemics are caused by Type A influenza virus. Type A influenza virus has 2 types of envelope glycoproteins, hemagglutinin (HA) and neuraminidase (NA), and, based on the antigen type, HA is classified into 16 subtypes and NA into 9 subtypes.

In the present invention, the antigens derived from Types A and B influenza viruses are preferably used to be the above antigen derived from an infectious disease. The subtype of Type A and Type B influenza viruses described above is not limited, and may be any of the subtypes isolated so far or subtypes to be isolated in a future.

In the present invention, the antigen derived from influenza viruses is not limited insofar as it is at least part of the many components composing the above influenza viruses. Examples include an inactivated whole virus in which a purified virus particle is inactivated with an organic solvent/surfactant or other reagents, or a virus subunit prepared by removing impurities from the inactivated whole virus and purifying HA and/or NA, and the like. The HA subunit or inactivated whole virus is preferable in light of the immunogenicity. The inactivated whole virus is preferably inactivated using formalin, or the like. The HA subunit (split), having very few impurities and requiring an adjuvant, is particularly effective.

The method for preparing the influenza virus antigen is not limited and any known method is used with no limitation. Examples include a method in which a virus strain isolated from an influenza-infected animal or an influenza patient is caused to infect a hen's egg, or the like, and incubated in a routine manner, thereby preparing an antigen from the purified undiluted virus solution. Alternatively, an antigen derived from a virus prepared in culture cells using a genetic engineering technique may also be used.

The vaccine composition of the present invention may contain the antigen derived from an infectious disease in an effective amount, but, preferably contains in an amount, for example, ranging from 0.001 to 1000 µg to the total amount thereof per individual per administration. The amount is more preferably 0.01 to 100 µg and still more preferably 0.1 to 50µ. An amount below 0.001 µg may result in the insufficient function to be a preventive or therapeutic agent for infectious diseases, whereas an amount exceeding 1000 µg may raise a safety issue. Additionally, the term "per individual" refers to any mammals and a human is preferred.

The vaccine composition of the present invention contains at least one selected from the group consisting of a toll-like receptor 4 (TLR4) agonist, a toll-like receptor 2/6 (TLR2/6) agonist, and cyclic dinucleotide, or a derivative or salt thereof.

These compounds serve as adjuvants in the vaccine composition of the present invention.

Preferable examples of the toll-like receptor 4 (TLR4) agonist include lipopolysaccharide, or salt thereof. Additionally, the term "lipopolysaccharide" is intended to include, in addition to lipopolysaccharide, derivatives thereof as long as they maintain properties of lipopolysaccharide. The term "salt" refer to any organic acid salt or inorganic acid salt and a pharmaceutically acceptable salt is preferred.

The lipopolysaccharide may be an extract from the cell wall of gram-negative bacteria or a modified product thereof, or a synthetic product.

Examples of the gram-negative bacteria include *Escherichia* sp., *Shigella* sp., *Salmonella* sp., *Klebsiella* sp., *Proteus* sp., *Yersinia* sp., *V. cholerae* sp., *Vparahaemolyticus* sp., *Haemophilus* sp., *Pseudomonas* sp., *Legionella* sp., *Bordetella* sp., *Brucella* sp., *Francisella* tularensis sp., *Bacteroides* sp., *Neisseria* sp., *Chlamydia* sp., *Plesiomonas* sp., *Prophyromonas* sp., *Pantoea* sp., *Agrobacterium* sp., *Stenortophomonas* sp., *Enterobacter* sp., *Acetobacter* sp., *Xanthomonas* sp., *Zymomonas* sp., and the like.

Preferable gram-negative bacteria among them are those derived from *Escherichia* sp., *Salmonella* sp., *Pantoea* sp., *Acetobacter* sp., *Zymomonas* sp., *Xanthomonas* or *Enterobacter* sp. These bacteria have been used in many food products and herbal medicine for many years and the safety in the living body is guaranteed. The *Pantoea* bacteria, in particular, are currently used as health food products and assure more effectiveness. The extracts derived from these bacteria or modified products thereof may also be used without further treatment.

When the lipopolysaccharide is used in the form of an extract from the cell wall of the above gram-negative bacteria or a purified lipopolysaccharide, the safety in the living body should generally be considered and a modified product may also be used for the purpose of detoxifying them. On the other hand, *Acetobacter* sp. (*Acetobacter aceti, Acetobacter xylinum, Acetobacter orientalis*, or the like), *Zymomonas* sp. (*Zymomonas mobilis*, or the like), *Xanthomonas* sp. (*Xanthomonas campestris*, or the like), *Enterobacter* sp. (*Enterobacter cloacae*, or the like), and *Pantoea* sp. (*Pantoea agglomerans*, or the like) have been used in many food products and herbal medicine for many years, and the safety in the living body is guaranteed. The extracts derived from these bacteria or purified lipopolysaccharide may also be used without further treatment.

The toll-like receptor 4 (TLR4) agonist may be a derivative of the lipopolysaccharide and examples include lipid A wherein the polysaccharide moiety is removed from the lipopolysaccharide or monophosphoryl lipid A, 3 de-acylated MPL, and the like, and salts thereof.

The lipid A wherein the polysaccharide moiety is removed from the lipopolysaccharide may be an isolate derived from the above gram-negative bacteria, or a product synthesized so as to have the same structure as the isolate derived from the above gram-negative bacteria.

Preferably used examples of the lipid A modified product are dephosphorylated monophosphoryl lipid (MPL) or salt thereof. Additionally, the term "monophosphoryl lipid (MPL)" is intended to include, in addition to monophosphoryl lipid (MPL), derivatives thereof as long as they maintain properties of lipopolysaccharide.

In particular, 3 de-acylated monophosphoryl lipid (3D-MPL) which has been already used as an adjuvant for the medical purpose, or the non-deacylated synthetic glucopyranosyl lipid proposed in the US Patent Application Ser. No. 2010/0310602 specification are preferable in light of the safety in the living body.

*Salmonella* bacteria, previously used and are safe, are also preferably used as the monophosphoryl lipid.

The toll-like receptor 2/6 (TLR2/6) agonist preferably contains, for example, diacylated lipopeptide, or a derivative or salt thereof.

The diacylated lipopeptide preferably contains at least one selected from the group consisting of previously used and thus safe $Pam_2CSK_4$, MALP-2 and FSL-1, or a derivative or salt thereof.

The toll-like receptor 2/6 (TLR2/6) agonist may be an extract from mycoplasma cell membrane or a modified product thereof, or a synthetic product.

Examples of the mycoplasma include *Mycoplasma pneumoniae*, *Mycoplasma genitalium*, *Mycoplasma hominis*, *Ureaplasma*, *Mycoplasma salivarium*, *Mycoplasma fermentans*, *Mycoplasma gallisepticum*, *Mycoplasma hyopneumoniae*, *Mycoplasma laboratorium*, *Mycoplasma mycoides*, *Mycoplasma ovipneumoniae*, and the like.

When the toll-like receptor 2/6 (TLR2/6) agonist is used in the form of an extract from the mycoplasma cell membrane or a purified diacylated lipopeptide, the safety in the living body should generally be considered and a modified product may also be used for the purpose of detoxifying them.

The cyclic dinucleotide may be cyclic bis-dipurine nucleotide, or a derivative or salt thereof and preferable examples include, in light of the safety, c-di-GMP, c-di-AMP, or a derivative or salt thereof.

The above TLR4 agonist, TLR2/6 agonist and c-di-GMP each sufficiently function to serve as a sublingual adjuvant. The TLR4 agonist, particularly, is available at a low price and has been used to human. For example, *Pantoea* LPS, one of the above TLR4 agonists, has been commonly used in health food products and offers a benefit of being easily adaptable to human.

The vaccine composition of the present invention may preferably contain the above 3 adjuvants (TLR4, TLR2/6, cyclic dinucleotide) in an amount, for example, ranging from 0.1 μg to 100 mg to the total amount thereof. An amount below 0.1 μg may result in the insufficient function to be a preventive or therapeutic agent for infectious diseases, whereas an amount exceeding 100 mg may raise a safety issue. More preferable lower limit content of the above adjuvants is 0.3 μg, and more preferable upper limit content is 50 mg.

Additionally, the vaccine composition of the present invention may use other conventionally used known adjuvants in combination with these adjuvants insofar as the composition contains at least one adjuvant selected from the group consisting of the above three adjuvants.

The vaccine composition of the present invention may be prepared by adding other components (e.g., phosphate buffer, and the like) as necessary to the above antigen derived from an infectious disease and the adjuvants and mixing with stirring by a known method.

The vaccine composition of the present invention may also be formulated into a solution, a solid preparation or a spray, and suitably use, if desired, excipient, binder, perfume, flavor, sweetener, colorant, preservative, antioxidant, stabilizer, surfactant, and/or the like, in addition to the materials described above.

These additives are not limited and the conventionally used known materials may be used.

The solid preparation herein encompasses tablets, coated tablets, powders, granules, fine granules, orally disintegrating tablet, oral patches, jellies and films, and is not limited insofar as it is a solid preparation to be administered to the oral cavity mucosa or sublingual mucosa.

The vaccine composition of the present invention is administered to the oral cavity of human or animals (mammals, avian, or the like), but the oral cavity administration is preferably sublingual mucosa administration. As described earlier, the oral cavity mucosa is generally not likely to develop immunity, and the activation of immunity, even if the immunotolerance is developed, has been considered to be difficult. However, the vaccine composition of the present invention uses the specific adjuvants described above in combination with at least one antigen derived from an infectious disease, and thus effectively induces the systemic immune response and mucosal immune response even when administered to the oral cavity mucosa.

The sublingual mucosa administration also enables the composition to be less susceptible to the influences of gastric juice and proteases unlike the antigen administration to the gastrointestinal mucosa; and to be free of potential critical adverse effects such as acute encephalopathy, or the like; to be easy to practice on the elderly, infant, or the like; and to provide stable effects uninterrupted by physical factors such as nasal mucus, or the like, unlike the antigen administration to the transnasal mucosa.

The method for administering the vaccine composition of the present invention is as described earlier. The dose is determined in accordance with animal species, age, sex, body weight to be administered, and the like, and, for example, 0.1 μg to 50 μg is typically administered once or more than twice when HA is used as the antigen derived from an infectious disease. The vaccine composition is preferably administered in several doses, and the composition in this case is preferably administered with 1 to 4 week intermittent. To use inactivated whole virus as the antigen derived from an infectious disease, the dose is determined in terms of HA. Additionally, the HA weight is a value measured by SRD titer or the Lowry method.

Advantageous Effects of Invention

The vaccine composition of the present invention uses the specific adjuvants described above in combination with at least one antigen derived from an infectious disease, and thus effectively induces the systemic immune response and mucosal immune response when administered to the oral cavity mucosa, particularly sublingual mucosa.

DESCRIPTION OF EMBODIMENTS

Hereinafter, the present invention is described further in detail with reference to the following examples, but is not limited thereto.

Example 1

Phosphate buffer (Nacalai Tesque, Inc.) was added to 76.3 µL (236 µg/mL) of an influenza HA antigen-containing solution (A/IvPR8/34(H1N1), The Research Foundation for Microbial Diseases of Osaka University) and 30 µL (1 mg/mL) of a solution containing $E.\ Coli$ lipopolysaccharide (Nacalai Tesque, Inc.) to prepare 120 µL of a vaccine composition.

Five mice (7-week old, C57BL/6 female mice, Japan SLC, Inc.) prepared in advance were anaesthetized (Somnopentyl, Kyoritsu Seiyaku Corporation), and 20 µL of the prepared vaccine composition was sublingually administered to each of the mice.

1 week later from the administration, the mice were anaesthetized again and 20 µL of the prepared vaccine composition was sublingually administered to each of the mice.

Another week later from the second administration, the serum and nasal wash were collected from the mice, and the serum influenza HA-specific IgG titer and nasal wash influenza HA-specific IgA titer were measured by ELISA. The measurement method is described later in detail.

Examples 2 to 6

Vaccine compositions were prepared in the same manner as Example 1, except that, in place of the $E.\ coli$ lipopolysaccharide, $Pantoea$ lipopolysaccharide (macrophi inc.) was used in Example 2, glucopyranosyl lipid (MPLAs, InvivoGen) was used in Example 3, FSL-1 (InvivoGen) was used in Example 4, Pam$_2$CSK$_4$ (InvivoGen) was used in Example 5 and c-di-GMP (Cyclic diguanosine monophosphate, Biolog Inc.) was used in Example 6. The test was carried out by the same procedure as Example 1 in the doses shown in Table 1.

Comparative Example 1

Five mice (7-week old, C57BL/6 female mice, Japan SLC, Inc.) prepared in advance were anaesthetized, 120 µL of phosphate buffer (Nacalai Tesque, Inc.) was prepared and 20 µL thereof was sublingually administered to each of the mice. The test was carried out by the same subsequent procedure as Example 1.

Comparative Example 2

In place of the phosphate buffer, phosphate buffer (Nacalai Tesque, Inc.) was added to 76.3 µL (236 µg/mL) of an influenza HA antigen-containing solution (A/IvPRB/34 (H1N1), The Research Foundation for Microbial Diseases of Osaka University) to prepare 120 µL of a vaccine composition. The test was carried out by the same subsequent procedure as Example 1 in the dose shown in Table 1.

Comparative Examples 3 to 9

Vaccine compositions were prepared in the same manner as Comparative Example 2, except that, in addition to the influenza HA antigen-containing solution (A/IvPR8/34 (H1N1), The Research Foundation for Microbial Diseases of Osaka University), peptidoglycan (PGN derived from $Salmonella$, InvivoGen) was used in Comparative Example 3, zymosan (Nacalai Tesque, Inc.) was used in Comparative Example 4, Pam$_3$CSK$_4$ (InvivoGen) was used in Comparative Example 5, Poly (I:C) (InvivoGen) was used in Comparative Example 6, flagellin (InvivoGen) was used in Comparative Example 7, imiquimod (InvivoGen) was used in Comparative Example 8 and CpG (InvivoGen) was used in Comparative Example 9. The test was carried out by the same procedure as Example 1 in the doses shown in Table 1.

TABLE 1

| | Antigen | | Adjuvant | |
|---|---|---|---|---|
| No. | Dose (µg/body/ time) | Ligand | Substance name | Dose (µg/body/ time) |
| Example 1 | 3 | TLR4 | $E.\ coli$ LPS | 5 |
| Example 2 | 3 | TLR4 | $Pantoea$ LPS | 5 |
| Example 3 | 3 | TLR4 | GLA | 5 |
| Example 4 | 3 | TLR2/6 | FSL-1 | 5 |
| Example 5 | 3 | TLR2/6 | Pam$_2$CSK$_4$ | 5 |
| Example 6 | 3 | unclear | c-di-GMP | 138 |
| Comparative Example 1 | — | — | — | — |
| Comparative Example 2 | 3 | — | — | — |
| Comparative Example 3 | 3 | TLR2 | PGN | 100 |
| Comparative Example 4 | 3 | TLR2/Dectin1 | zymosan | 5 |
| Comparative Example 5 | 3 | TLR2/1 | Pam$_3$CSK$_4$ | 5 |
| Comparative Example 6 | 3 | TLR3 | poly I:C | 5 |
| Comparative Example 7 | 3 | TLR5 | flagelin | 5 |
| Comparative Example 8 | 3 | TLR7 | imiquimod | 5 |
| Comparative Example 9 | 3 | TLR9 | CpG | 5 |

Examples 7 to 9

In addition to 19 µL, (236 µg/mL) of the influenza HA antigen-containing solution (A/IvPR8/34(H1N1), The Research Foundation for Microbial Diseases of Osaka University), phosphate buffer (Nacalai Tesque, Inc.) was added to 30 µL, (1 mg/mL) of glucopyranosyl lipid (MPLAs, InvivoGen) to prepare 120 µL of a vaccine composition in Example 7. 20 µL thereof was sublingually administered to the mice (7-week old BALE/c female mice, Japan SLC, Inc.) under anaesthesia. In place of the glucopyranosyl lipid used in Example 7, FSL-1 (InvivoGen) was used in Example 8, and c-di-GMP (Cyclic diguanosine monophosphate, Biolog Inc.) was used in Example 9 to prepare vaccine compositions. The doses are as shown in Table 2. The test was carried out by the same procedure as Example 1 after the preparation, except that the mouse type was different.

Comparative Example 10

Phosphate buffer (Nacalai Tesque, Inc.) was added to 19 µL (236 µg/mL) of the influenza HA antigen-containing solution (A/IvPR8/34(H1N1), The Research Foundation for Microbial Diseases of Osaka University) to prepare 120 µL of a vaccine composition. The dose was as shown in Table 2. The test was carried out by the same procedure as Example 1 after the preparation, except that BALE/c mice were used.

Comparative Examples 11 and 12

In addition to 76.3 µL (236 µg/mL) of the influenza HA antigen-containing solution (A/IvPR8/34(H1N1), The Research Foundation for Microbial Diseases of Osaka University), in Comparative Example 11, phosphate buffer (Nacalai Tesque, Inc.) was added to 30 µL (20 mg/mL) of peptidoglycan (PGN derived from *Salmonella*, InvivoGen) to prepare 120 µL of a vaccine composition. In place of the peptidoglycan used in Comparative Example 11, Pam₃CSK₄ (InvivoGen) was used in Comparative Example 12 to prepare a vaccine composition. The doses were as shown in Table 2. The test was carried out by the same procedure as Example 1 after the preparation, except that BALB/c mice were used.

TABLE 2

| | Antigen | | Adjuvant | |
|---|---|---|---|---|
| No. | Type | Dose (µg/body/time) | Ligand | Substance name | Dose (µg/body/time) |
| Example 7 | A/IvPR8/34(H1N1) | 0.75 | TLR4 | GLA | 5 |
| Example 8 | A/IvPR8/34(H1N1) | 0.75 | TLR2/6 | FSL-1 | 5 |
| Example 9 | A/IvPR8/34(H1N1) | 0.75 | unclear | c-di-GMP | 138 |
| Comparative Example 10 | A/IvPR8/34(H1N1) | 0.75 | — | — | — |
| Comparative Example 11 | A/IvPR8/34(H1N1) | 0.75 | TLR2 | PGN | 100 |
| Comparative Example 12 | A/IvPR8/34(H1N1) | 0.75 | TLR2/1 | Pam₃CSK₄ | 5 |

Example 10

Phosphate buffer (Nacalai Tesque, Inc.) and 60 µL (1 mg/mL) of lipopolysaccharide derived from *Pantoea* (macrophi inc.) were added to 152.6 µL (236 µg/mL) of the influenza HA antigen-containing solution (A/IvPR8/34 (H1N1), The Research Foundation for Microbial Diseases of Osaka University), The Research Foundation for Microbial Diseases of Osaka University) to prepare 240 µL of a vaccine composition.

Ten mice (7-week old, BALB/c female mice, Japan SLC, Inc.) prepared in advance were anaesthetized and 20 µL of the prepared vaccine composition was sublingually administered to each of the mice.

1 week later from the administration, the mice were anaesthetized again and 20 µL of the prepared vaccine composition was sublingually administered to each of the mice.

Another week later from the second administration, the mice were infected with the lethal dose of influenza virus (A/IvPRB/34(H1N1) and monitored for the following 2 weeks to measure the survival rates. The measurement method is described later in detail.

Comparative Examples 13 and 14

In Comparative Example 13, a solution containing only the influenza HA antigen-containing solution (A/IvPR8/34 (H1N1), The Research Foundation for Microbial Diseases of Osaka University) was prepared, and in Comparative Example 14, a phosphate buffer was prepared. The test was carried out by the same procedure as Example 10 in the doses shown in Table 3.

TABLE 3

| | Antigen | | Adjuvant | | |
|---|---|---|---|---|---|
| No. | Type | Dose (µg/body/time) | Ligand | Substance name | Dose (µg/body/time) |
| Example 10 | A/IvPR8/34(H1N1) | 3 | TLR4 | *Pantoea* LPS | 5 |
| Comparative Example 13 | A/IvPR8/34(H1N1) | 3 | — | — | — |
| Comparative Example 14 | — | — | — | — | — |

Example 11

Phosphate buffer (Nacalai Tesque, Inc.) and 30 µL (1 mg/mL) of lipopolysaccharide derived from *Pantoea* (macrophi inc.) were added to 10.1 µL (1776 µg/mL) of an influenza HA antigen-containing inactivated whole virus solution (A/California/7/2009(H1N1), The Research Foundation for Microbial Diseases of Osaka University) to prepare 120 µL of a vaccine composition.

The test was carried out by the same procedure as Example 1 in the dose shown in Table 4.

Comparative Example 14

In Comparative Example 14, a solution containing only the influenza HA antigen-containing inactivated whole virus solution (A/California/7/2009(H1N1)) was prepared. The test was carried out by the same procedure as Example 1 in the dose shown in Table 4.

TABLE 4

| | Antigen | | Adjuvant | | |
|---|---|---|---|---|---|
| No. | Type | Dose (µg/body/time) | Ligand | Substance name | Dose (µg/body/time) |
| Example 11 | Inactivated whole virus (A/California/7/2009(H1N1)) | 3 | TLR4 | *Pantoea* LPS | 5 |
| Comparative Example 14 | Inactivated whole virus (A/California/7/2009(H1N1)) | 3 | — | — | — |
| Comparative Example 1 | — | — | — | — | — |

Example 12

Phosphate buffer (Nacalai Tesque, Inc.) and 30 μL (1 mg/mL) of lipopolysaccharide derived from *Pantoea* (macrophi inc.) were added to 36 μL (500 μg/mL) of an influenza HA antigen-containing solution (A/California/7/2009 (H1N1), The Research Foundation for Microbial Diseases of Osaka University) to prepare 120 μL of a vaccine composition.

The test was carried out by the same procedure as Example 1 in the dose shown in Table 5.

Example 13

In place of the lipopolysaccharide derived from *Pantoea* used in Example 12, c-di-GMP (Cyclic diguanosine monophosphate, Biolog Inc.) was used in Example 13 to prepare a vaccine composition in the same manner as Example 12. The test was carried out by the same procedure as Example 1 in the dose shown in Table 5.

Comparative Example 15

In place of the lipopolysaccharide derived from *Pantoea* used in Example 12, imiquimod (InvivoGen) was used in Comparative Example 15 and the test was carried out by the same procedure as Example 1 in the dose shown in Table 5.

Comparative Example 16

In place of the lipopolysaccharide derived from *Pantoea* used in Example 12, a solution containing only the influenza HA antigen-containing solution (A/IvPR8/34(H1N1), The Research Foundation for Microbial Diseases of Osaka University) was prepared without adding any other components in Comparative Example 16. The test was carried out by the same procedure as Example 1 in the dose shown in Table 5.

TABLE 5

| | Antigen | | Adjuvant | | |
|---|---|---|---|---|---|
| No. | Type | Dose (μg/ body/ time) | Ligand | Substance name | Dose (μg/ body/ time) |
| Example 12 | A/California/ 7/2009(H1N1) | 3 | TLR4 | *Pantoea* LPS | 5 |
| Example 13 | A/California/ 7/2009(H1N1) | 3 | unclear | c-di-GMP | 5 |
| Comparative Example 15 | A/California/ 7/2009(H1N1) | 3 | TLR7 | imiquimod | 5 |
| Comparative Example 16 | A/California/ 7/2009(H1N1) | 3 | — | — | — |
| Comparative Example 1 | — | — | — | — | — |

Example 14

Phosphate buffer (Nacalai Tesque, Inc.) and 30 μL (1 mg/mL) of lipopolysaccharide derived from *Pantoea* (macrophi inc.) were added to 33.7 μL (534 μg/mL) of an influenza HA antigen-containing solution (A/Victria/361/2009(H3N2), The Research Foundation for Microbial Diseases of Osaka University) to prepare 120 μL of a vaccine composition. The test was carried out by the same procedure as Example 1 in the dose shown in Table 6.

Example 15

Phosphate buffer (Nacalai Tesque, Inc.) and 30 μL (1 mg/mL) of lipopolysaccharide derived from *Pantoea* (macrophi inc.) were added to 47.4 μL (380 μg/mL) of the influenza HA antigen-containing solution (B/Brisbane/60/2008, The Research Foundation for Microbial Diseases of Osaka University) to prepare 120 μL of a vaccine composition. The test was carried out by the same procedure as Example 1 in the dose shown in Table 6.

TABLE 6

| | Antigen | | Adjuvant | | |
|---|---|---|---|---|---|
| No. | Type | Dose (μg/ body/ time) | Ligand | Substance name | Dose (μg/ body/ time) |
| Example 12 | A/California/ 7/2009(H1N1) | 3 | TLR4 | *Pantoea* LPS | 5 |
| Example 14 | A/Victoria/ 361/2009(H3N2) | 3 | TLR4 | *Pantoea* LPS | 5 |
| Example 15 | B/Brisbane/ 60/2008 | 3 | TLR4 | *Pantoea* LPS | 5 |
| Comparative Example 16 | A/California/ 7/2009(H1N1) | 3 | — | — | — |
| Comparative Example 1 | — | — | — | — | — |

Example 16

A vaccine composition was prepared in the same manner as Example 12. More specifically, phosphate buffer (Nacalai Tesque, Inc.) and 30 μL (1 mg/mL) of lipopolysaccharide derived from *Pantoea* (macrophi inc.) were added to 36 μL (500 μg/mL) of an influenza HA antigen-containing solution (A/California/7/2009(H1N1), The Research Foundation for Microbial Diseases of Osaka University) to prepare 120 μL of a vaccine composition.

The test was carried out by the same procedure as Example 1 in the dose shown in Table 7, except that BALB/c mice were used.

Example 17

Phosphate buffer (Nacalai Tesque, Inc.) and 30 μL (1 mg/mL) of lipopolysaccharide derived from *Pantoea* (macrophi inc.) were added to 18 μL (1 mg/mL) of OVA (Ovalbumin, Sigma-Aldrich Co. LLC.) to prepare 120 μL of a vaccine composition.

The test was carried out by the same procedure as Example 1 in the dose shown in Table 7, except that BALB/c mice were used.

Comparative Example 17

In place of the lipopolysaccharide derived from *Pantoea* used in Example 16, a solution containing only the influenza HA antigen-containing solution (A/IvPR8/34(H1N1), The Research Foundation for Microbial Diseases of Osaka University) was prepared without adding any other components in Comparative Example 17. The test was carried out by the same procedure as Example 1 in the dose shown in Table 7, except that BALB/c mice were used.

Comparative Example 18

In place of the lipopolysaccharide derived from *Pantoea* used in Example 17, a solution containing only OVA (Ovalbumin, Sigma-Aldrich Co. LLC.) was prepared without adding any other components in Comparative Example 18. The test was carried out by the same procedure as Example 1 in the dose shown in Table 7, except that BALB/c mice were used.

TABLE 7

| | Antigen | | Adjuvant | | |
|---|---|---|---|---|---|
| No. | Type | Dose (μg/body/time) | Ligand | Substance name | Dose (μg/body/time) |
| Example 16 | A/California/7/2009(H1N1) | 3 | TLR4 | *Pantoea* LPS | 5 |
| Example 17 | Ovalbumin (OVA) | 3 | TLR4 | *Pantoea* LPS | 5 |
| Comparative Example 17 | A/California/7/2009(H1N1) | 3 | — | — | — |
| Comparative Example 18 | Ovalbumin (OVA) | 3 | — | — | — |

Test Method

The systemic immune response was evaluated by measuring the mouse serum influenza HA- or OVA-specific IgG titer. The mucosal immune response was evaluated by measuring the mouse nasal wash influenza HA- or OVA-specific IgA titer. Each of the evaluation method is described below. Each of the evaluation results are shown in FIGS. 1 to 13 (except FIG. 5).

Figure 5:
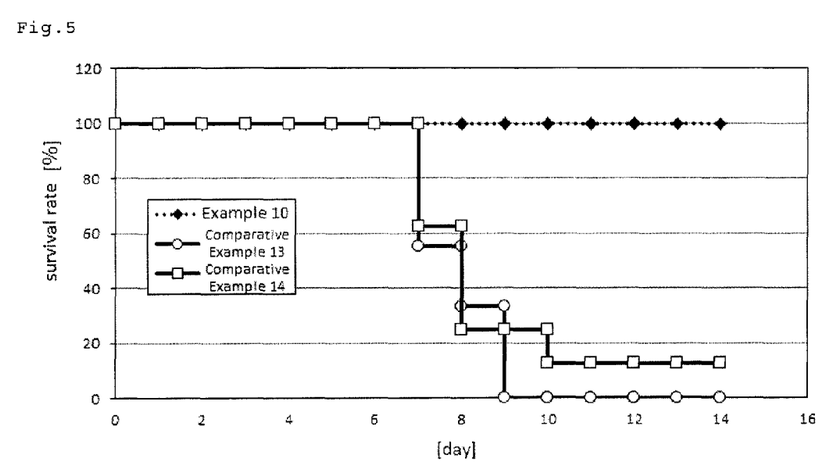
FIG. 5 is a graph showing the survival rates of mice infected with influenza virus in Example 10, Comparative Examples 13 and 14.

A virus infection experiment was meanwhile carried out to reveal the vaccine efficacy by infecting the mice with the influenza virus. The evaluation results are shown in FIG. 5.

Measurement Method of Mouse Serum Influenza HA-Specific IgG Titer (ELISA)

100 μL of each influenza HA (e.g., A/IvPR8/34(H1N1) influenza HA antigen solution for measuring an A/IvPR8/34(H1N1)-specific IgG antibody titer) diluted with carbonate buffer or an OVA-containing solution (5 μg/mL) was added to an ELISA 96-well plate and allowed to stand overnight.

The wells were washed 3 times with a wash (Tween20-containing PBS) prepared in advance, and 200 μL of a blocking solution wherein a blocking agent (Block Ace, DS Pharma Biomedical Co., Ltd.) was diluted to 4 g/100 mL with purified water was added to each well, which was allowed to stand at room temperature for 2 hours. Subsequently, the wells were washed 3 times with the wash (Tween20-containing PBS).

The serum collected from the mice in advance was centrifuged at 4° C. at 3000 G for 10 minutes, 300 μL of phosphate buffer (Nacalai Tesque, Inc.) was added to 20 μL of the supernatant to prepare a diluted serum solution.

Using a solution wherein a blocking agent (Block Ace, DS Pharma Biomedical Co., Ltd.) wad diluted to 0.4 g/100 mL with phosphate buffer (Nacalai Tesque, Inc.), the above diluted serum solution was diluted two-fold in 16 steps, and 50 μL of the solution was added and allowed to stand at room temperature for 2 hours.

The wells were washed 3 times with a wash (Tween20-containing PBS), an HRP-labeled anti-mouse IgG antibody (Goat-anti-mouse IgG Fc HRP, BETHYL Laboratories, Inc.) was diluted 10000-fold with the solution wherein a blocking agent (Block Ace, DS Pharma Biomedical Co., Ltd.) was diluted to 0.4 g/100 mL with phosphate buffer (Nacalai Tesque, Inc.), and 100 μL each was added and allowed to stand at room temperature for 1 hour.

Subsequently, the wells were washed 3 times with the wash (Tween20-containing PBS) and 100 μL each of a TMB solution (ELISA POD TMB kit, Nacalai Tesque, Inc.) was added. 100 μL of a 1M sulfuric acid solution was added thereto and the 96-well plate was measured using a microplate reader (168-11135CAM, Bio-rad Laboratories, Inc.) for the 450 nm absorbance. The mouse serum IgG titers were determined in log 2 based on the absorbance at the time of step dilution.

Measurement Method of Mouse Nasal Wash Influenza HA-Specific IgA Titer (ELISA)

100 μL of each influenza HA (e.g., A/IvPR8/34(H1N1) influenza HA for measuring an A/IvPR8/34(H1N1)-specific IgA antibody titer) diluted with carbonate buffer or an OVA-containing solution (5 μg/mL) was added to an ELISA 96-well plate and allowed to stand overnight.

The wells were washed 3 times with a wash (Tween20-containing PBS) prepared in advance, and 200 μL of a blocking solution wherein a blocking agent (Block Ace, DS Pharma Biomedical Co., Ltd.) was diluted to 4 g/100 mL with purified water was added to each well, which was allowed to stand at room temperature for 2 hours.

The wells were subsequently washed 3 times with a wash (Tween20-containing PBS). The nasal washes collected from the mice were diluted two-fold in 12 steps with the solution wherein a blocking agent (Block Ace, DS Pharma Biomedical Co., Ltd.) wad diluted to 0.4 g/100 mL with phosphate buffer (Nacalai Tesque, Inc.), and 50 μL each of the solution was added and allowed to stand at room temperature for 2 hours.

The wells were washed 3 times with a wash (Tween20-containing PBS), an HRP-labeled anti-mouse IgA antibody (Goat-anti-mouse IgA Fc HRP, BETHYL Laboratories, Inc.) was diluted 10000-fold with the solution wherein a blocking agent (Block Ace, DS Pharma Biomedical Co., Ltd.) was diluted to 0.4 g/100 mL with phosphate buffer (Nacalai Tesque, Inc.), and 100 μL each thereof was added and allowed to stand at room temperature for 1 hour. Subsequently, the wells were washed 3 times with the wash (Tween20-containing PBS) and 100 μL each of a TMB solution (ELISA POD TMB kit, Nacalai Tesque, Inc.) was added. 100 μL of a 1M sulfuric acid solution was added thereto and the 96-well plate was measured using a microplate reader (168-11135CAM, Bio-rad Laboratories, Inc.) for the 450 nm absorbance. The mouse nasal wash IgA titers were determined in log 2 based on the absorbance at the time of step dilution.

A/IvPR8/34 (H1N1) Influenza Virus Infection Experiment to Mice (Survival Rate Measurement)

15 μL of diluted A/IvPR8/34 (H1N1) influenza virus was administered under anaesthesia to the vaccine-administered mice 1 week later from the final administration (10×LD50: 50% Lethal Dose). Defining the virus administration day as Day 0, the mice were monitored up to Day 14 to measure the survival rates.

Figure 1:
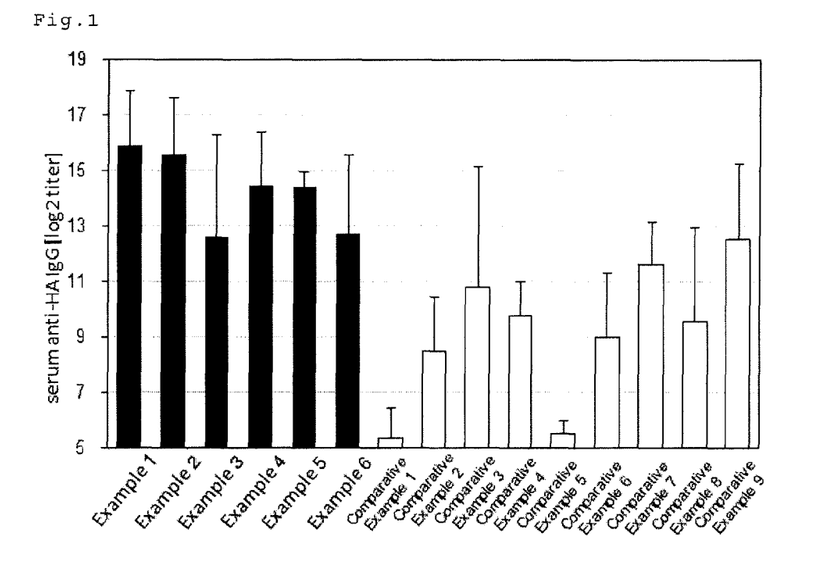
FIG. 1 is a graph showing the results of mouse serum influenza HA-specific IgG titer in Examples 1 to 6 and Comparative Examples 1 to 9.
Figure 2:
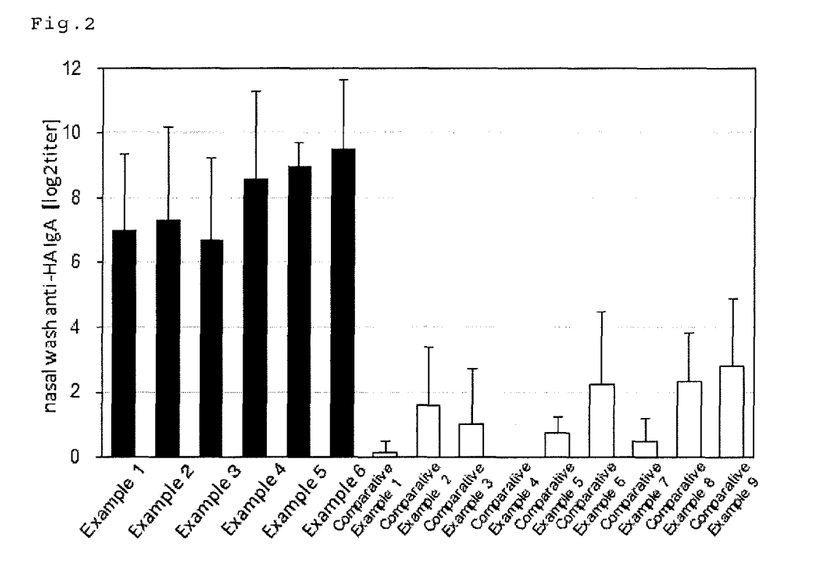
FIG. 2 is a graph showing the results of mouse nasal wash influenza HA-specific IgA titer in Examples 1 to 6 and Comparative Examples 1 to 9.

As shown in FIGS. 1 and 2, the influenza HA-specific IgG and IgA were produced in high yields in Examples 1 to 6, whereas the influenza-specific IgA was produced in low yields and the influenza HA-specific IgG was only somewhat produced in Comparative Examples 1 to 9. These results revealed that the TLR4 agonist and TLR2/6 agonist, cyclic dinucleotide are effective as adjuvants for inducing the mucosal immunity when sublingually administered.

Figure 3:
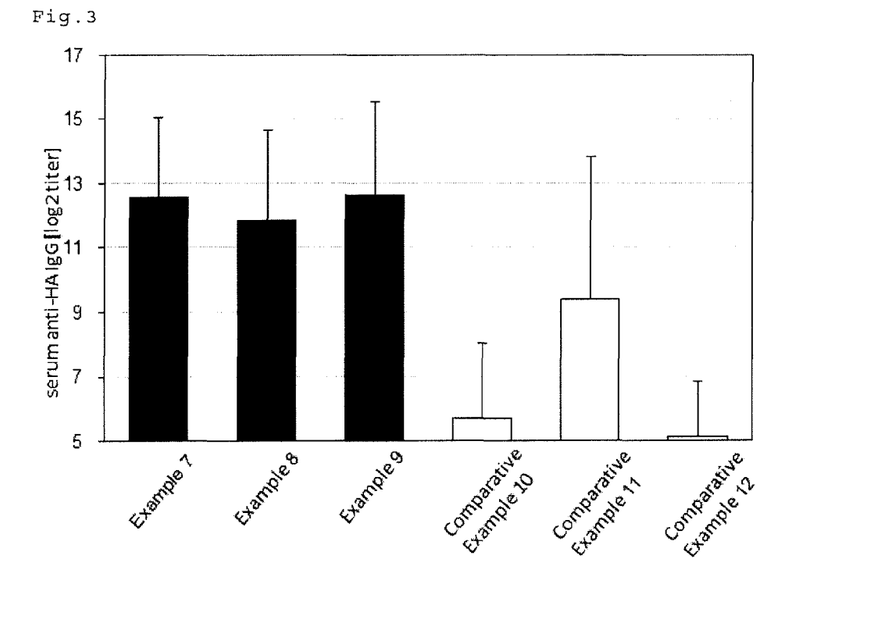
FIG. 3 is a graph showing the results of mouse serum influenza HA-specific IgG titer in Examples 7 to 9 and Comparative Examples 10 to 12.
Figure 4:
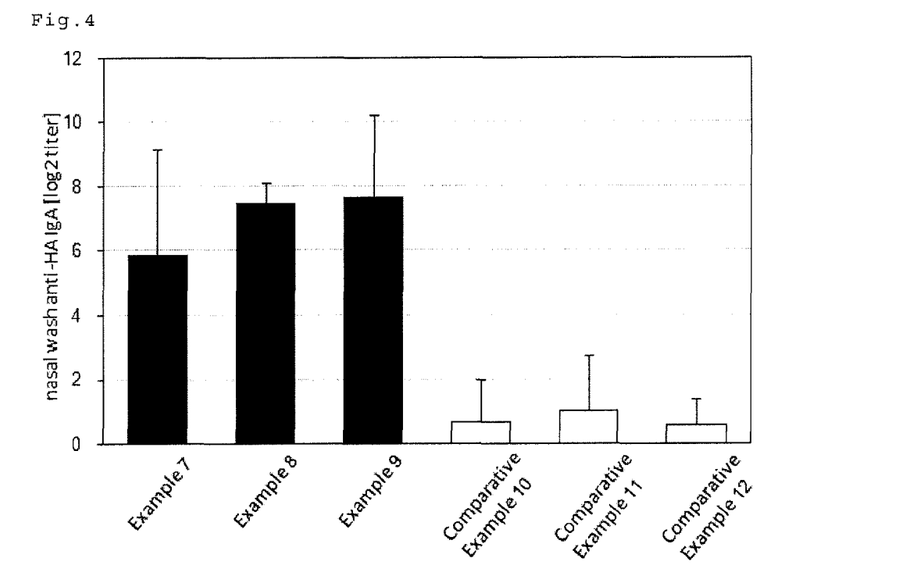
FIG. 4 is a graph showing the results of mouse nasal wash influenza HA-specific IgA titer in Examples 7 to 9 and Comparative Examples 10 to 12.

As shown in FIGS. 3 and 4, the comparison between Examples 7 to 9 and Comparative Examples 10 to 12 revealed that the sufficient systemic immunity and mucosal immunity are likely to be induced by the sublingual administration even in the system wherein the dose of influenza HA antigen was reduced to 0.75 μg.

As shown in FIG. 5, the comparison between Example 10 and Comparative Examples 13 and 14 revealed that the sublingual immunity provides the complete infection protection against the lethal dose of the influenza virus.

Figure 6:
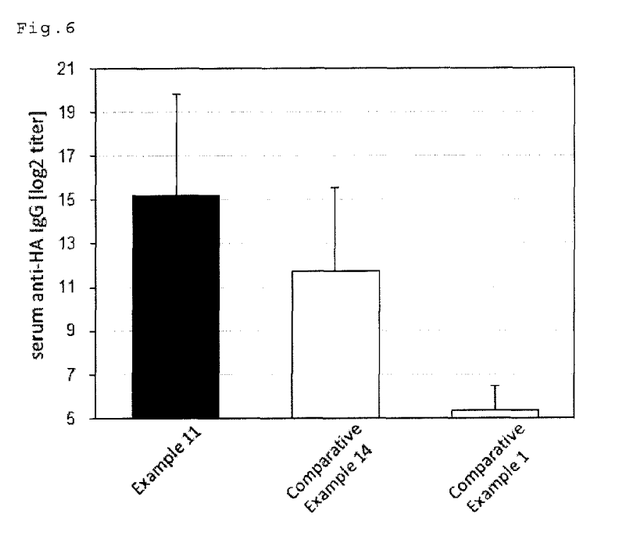
FIG. 6 is a graph showing the results of mouse serum influenza HA-specific IgG titer in Examples 11, Comparative Examples 1 and 14.
Figure 7:
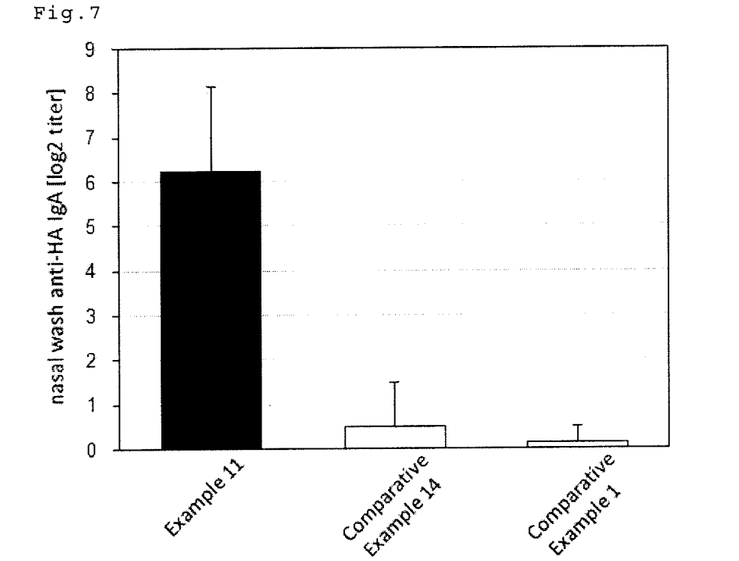
FIG. 7 is a graph showing the results of mouse nasal wash influenza HA-specific IgA titer in Examples 11, Comparative Examples 1 and 14.

As shown in FIGS. 6 and 7, the comparison between Example 11 and Comparative Examples 14 and 1 revealed that the sufficient systemic immunity and mucosal immunity are likely to be induced in the inactivated whole virus vaccine when the adjuvants are used.

Figure 8:
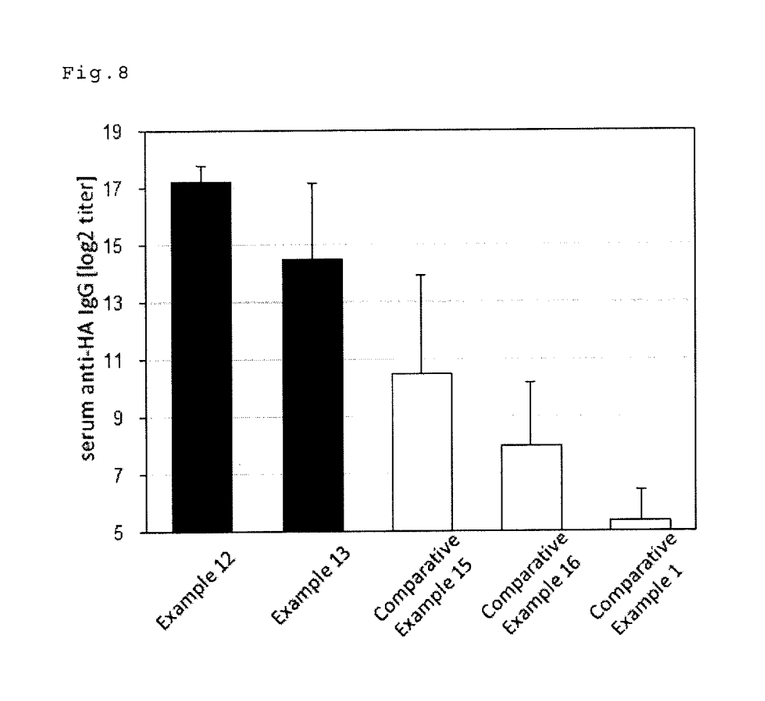
FIG. 8 is a graph showing the results of mouse serum influenza HA-specific IgG titer in Examples 12 and 13, Comparative Examples 15, 16 and 1.
Figure 9:
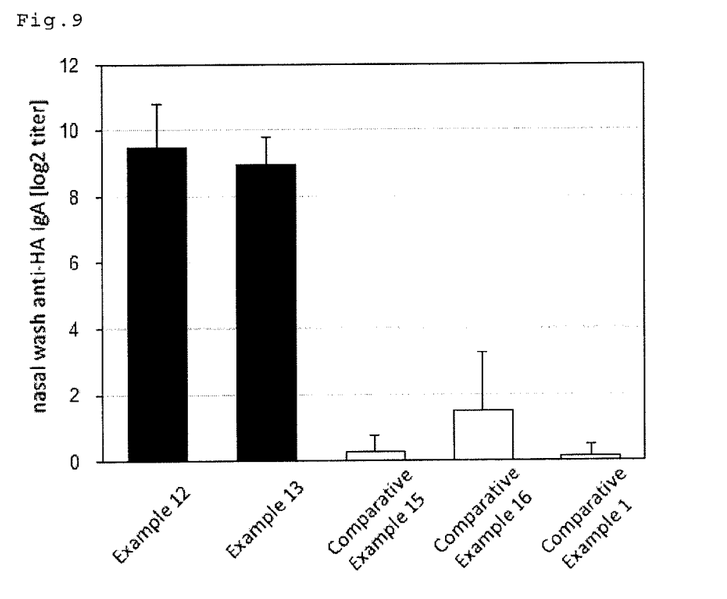
FIG. 9 is a graph showing the results of mouse nasal wash influenza HA-specific IgA titer in Examples 12 and 13, Comparative Examples 15, 16 and 1.

As shown in FIGS. 8 and 9, the comparison between Examples 12 and 13 and Comparative Examples 15, 16 and 1 revealed that the systemic immunity and mucosal immunity are likely to be induced in A/California/7/2009(H1N1), a seasonal influenza infectious to human.

Figure 10:
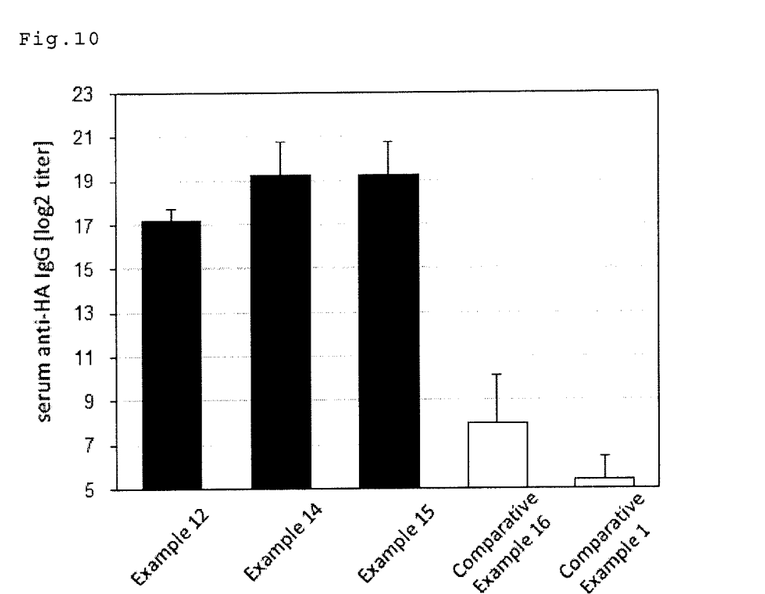
FIG. 10 is a graph showing the results of mouse serum influenza HA-specific IgG titer in Examples 12, 14 and 15, Comparative Examples 16 and 1.
Figure 11:
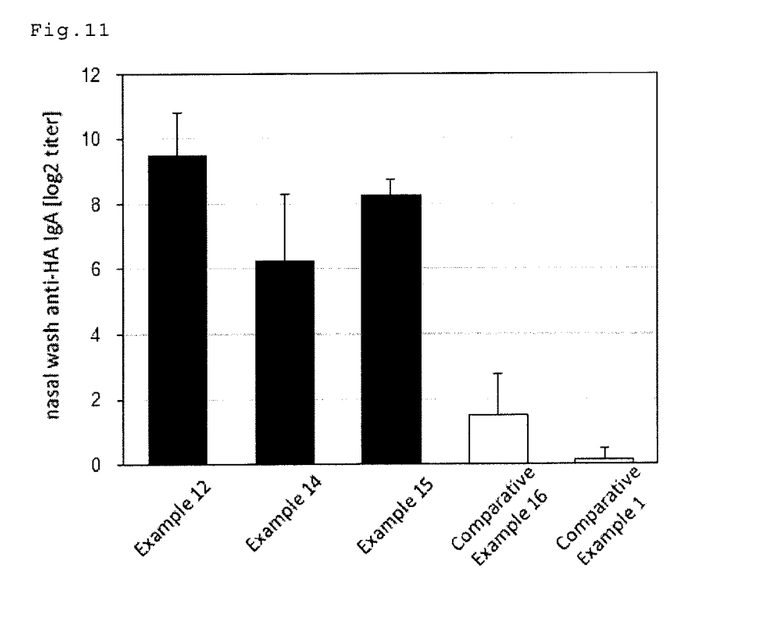
FIG. 11 is a graph showing the results of mouse nasal wash influenza HA-specific IgA titer in Examples 12, 14 and 15, Comparative Examples 16 and 1.

As shown in FIGS. 10 and 11, the comparison between Examples 12, 14 and 15 and Comparative Examples 16 and 1 revealed that the sublingual immunity is likely to induce the systemic immunity and mucosal immunity against different types of influenza viruses.

Figure 12:
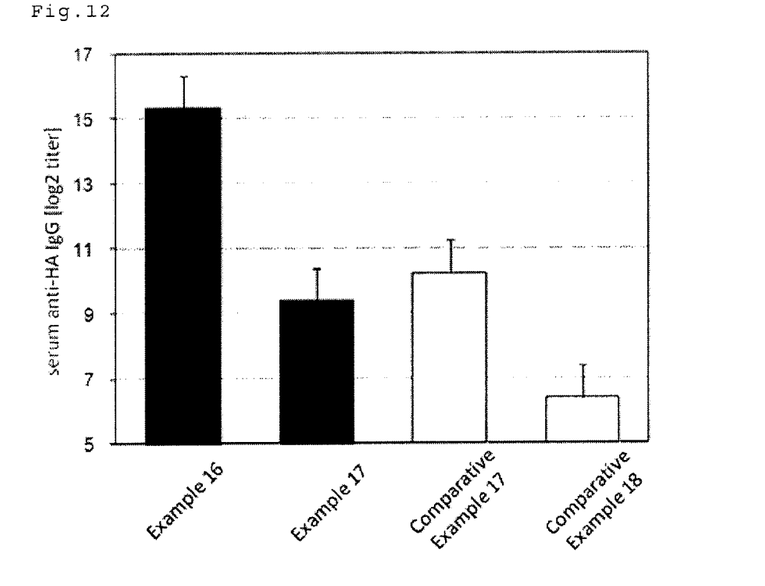
FIG. 12 is a graph showing the results of mouse serum influenza HA-specific IgG titer in Examples 16 and 17, Comparative Examples 17 and 18.
Figure 13:
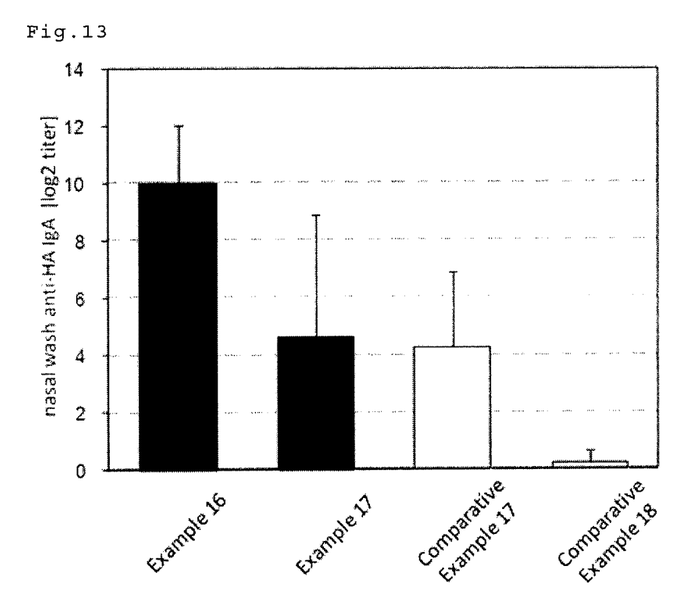
FIG. 13 is a graph showing the results of mouse nasal wash influenza HA-specific IgA titer in Examples 16 and 17, Comparative Examples 17 and 18.

As shown in FIGS. 12 and 13, the comparison between Examples 16 and 17 and Comparative Examples 17 and 18 revealed that the influenza HA-specific and OVA-specific systemic immunity and mucosal immunity are highly induced.

INDUSTRIAL APPLICABILITY

The vaccine composition of the present invention uses the specific adjuvants described above in combination with at least one antigen derived from an infectious disease, and thus effectively induces the systemic immune response and mucosal immune response even when administered to the oral cavity mucosa.

The invention claimed is:

1. A vaccine composition for administration to the oral cavity mucosa of a human or an animal, the vaccine composition comprising:
at least one antigen derived from an infectious disease, and an adjuvant-effective amount of lipopolysaccharide or salt thereof,
wherein the lipopolysaccharide or salt thereof is derived from *Pantoea*,
wherein the vaccine composition induces a mucosal immune response and a systemic immune response, the mucosal immune response being antigen-specific IgA antibody production, and the systemic immune response being antigen-specific IgG antibody production and antigen-specific cell-mediated immune production.

2. The vaccine composition according to claim 1, wherein the antigen derived from an infectious disease is an influenza virus-derived antigen.

3. The vaccine composition according to claim 2, wherein the influenza virus-derived antigen is hemagglutinin protein.

4. The vaccine composition according to claim 2, wherein the influenza virus-derived antigen is an inactivated whole virus.

5. The vaccine composition according to claim 1, wherein the vaccine composition is in the form of a solid dosage preparation, and further comprises at least one pharmaceutical additive.

6. The vaccine composition according to claim 5, wherein the vaccine composition is in the form of an orally disintegrating tablet.

7. A method for inducing mucosal antigen-specific IgA antibody production and a systemic antigen-specific IgG antibody production and antigen-specific cell-mediated immune production, comprising administering, to the oral cavity mucosa of a subject, a composition comprising:
at least one antigen derived from an infectious disease, and an adjuvant-effective amount of lipopolysaccharide or salt thereof, wherein the lipopolysaccharide is derived from *Pantoea*.

8. A vaccine composition for administration to the oral cavity mucosa of a human or an animal, the vaccine composition comprising:
at least one antigen derived from an infectious disease, and an adjuvant-effective amount of lipopolysaccharide or salt thereof,
wherein the lipopolysaccharide or salt thereof is derived from *Pantoea*, and
wherein the vaccine composition induces an antigen-specific immune response on administration to the oral cavity mucosa.

9. The method according to claim 7, wherein the vaccine composition is in the form of a solid dosage preparation, and further comprises at least one pharmaceutical additive.

10. The method according to claim 9, wherein the vaccine composition is in the form of an orally disintegrating tablet.

11. A method of vaccinating a human or animal subject comprising administering the vaccine composition according to claim 1 to the oral cavity mucosa of the human or animal subject.

* * * * *

UNITED STATES PATENT AND TRADEMARK OFFICE
CERTIFICATE OF CORRECTION

PATENT NO. : 9,498,527 B2
APPLICATION NO. : 13/856002
DATED : November 22, 2016
INVENTOR(S) : Masahiro Fukasaka et al.

Page 1 of 1

It is certified that error appears in the above-identified patent and that said Letters Patent is hereby corrected as shown below:

On the Title Page

Item (71) Applicants, please change "NITTO DENKO CORPORATION, Osaka (JP); OSAKA UNIVERSITY, Osaka (JP)" to -- NITTO DENKO CORPORATION, Osaka, (JP) --

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*